US006451860B1

(12) United States Patent
Young

(10) Patent No.: US 6,451,860 B1
(45) Date of Patent: Sep. 17, 2002

(54) METHODS FOR TREATING DEPRESSION AND OTHER DISORDERS USING OPTICALLY PURE (−)-BUPROPION

(75) Inventor: James W. Young, Palo Alto, CA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 10/076,645

(22) Filed: Feb. 19, 2002

Related U.S. Application Data

(62) Division of application No. 09/891,266, filed on Jun. 27, 2001, now Pat. No. 6,369,113, which is a division of application No. 09/553,029, filed on Apr. 20, 2000, now Pat. No. 6,277,887, which is a division of application No. 09/238,812, filed on Jan. 28, 1999, now Pat. No. 6,110,973.

(60) Provisional application No. 60/072,931, filed on Jan. 29, 1998.

(51) Int. Cl.[7] .............................................. A61K 31/35

(52) U.S. Cl. ......................................................... 514/649

(58) Field of Search ......................................... 514/649

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |
| 3,622,675 A | 11/1971 | Koppe et al. | |
| 3,630,200 A | 12/1971 | Higuchi | 128/260 |
| 3,819,706 A | 6/1974 | Mehta | 260/570.5 C |
| 3,845,770 A | 11/1974 | Theeuwes et al. | 128/260 |
| 3,885,046 A | 5/1975 | Mehta | 424/330 |
| 3,916,899 A | 11/1975 | Theeuwes et al. | 128/260 |
| 3,960,927 A | 6/1976 | Metcalf et al. | 260/471 A |
| 4,008,719 A | 2/1977 | Theeuwes et al. | 128/260 |
| 4,347,176 A | 8/1982 | Mehta | 260/112 B |
| 4,347,177 A | 8/1982 | Phillips | 260/112 B |
| 4,347,178 A | 8/1982 | Findlay et al. | 260/112 B |
| 4,347,257 A | 8/1982 | Stern | 424/330 |
| 4,347,382 A | 8/1982 | Scharver | 564/182 |
| 4,355,179 A | 10/1982 | Findlay et al. | 564/177 |
| 4,356,165 A | 10/1982 | Findlay et al. | 424/1 |
| 4,393,078 A | 7/1983 | Peck | 424/330 |
| 4,425,363 A | 1/1984 | Stern | 424/330 |
| 4,435,449 A | 3/1984 | Stern | 424/330 |
| 4,438,138 A | 3/1984 | Stern | 424/330 |
| 4,507,323 A | 3/1985 | Stern | 514/649 |
| 4,571,395 A | 2/1986 | Peck | 514/221 |
| 4,656,026 A | 4/1987 | Coffman et al. | 424/9 |
| 4,687,660 A | 8/1987 | Baker et al. | 424/465 |
| 4,769,027 A | 9/1988 | Baker et al. | 424/493 |
| 4,798,826 A | 1/1989 | Peck | 514/221 |
| 4,835,147 A | 5/1989 | Roberts | 514/178 |
| 4,868,344 A | 9/1989 | Brown | 568/812 |
| 4,895,845 A | 1/1990 | Seed | 514/252 |
| 4,935,429 A | 6/1990 | Dackis et al. | 514/288 |
| 4,935,439 A | 6/1990 | Kashman et al. | 514/475 |
| RE33,994 E | 7/1992 | Baker et al. | 424/465 |
| 5,217,987 A | 6/1993 | Berger | 514/416 |
| 5,358,970 A | 10/1994 | Ruff et al. | 514/649 |
| 5,427,798 A | 6/1995 | Ludwig et al. | 424/464 |
| 5,447,948 A | 9/1995 | Seibyl et al. | 514/393 |
| 5,512,593 A | 4/1996 | Dante | 514/410 |
| 5,541,231 A | 7/1996 | Ruff et al. | 514/649 |
| 5,731,000 A | 3/1998 | Ruff et al. | 424/451 |
| 5,753,712 A | 5/1998 | Pinkser | 514/649 |
| 5,763,493 A | 6/1998 | Ruff et al. | 514/617 |

FOREIGN PATENT DOCUMENTS

| | | |
|---|---|---|
| CA | 977777 | 11/1975 |
| CA | 977778 | 11/1975 |
| EP | 0 118 036 | 9/1984 |
| EP | 0 171 227 | 2/1986 |
| EP | 0 467 488 | 1/1992 |
| JP | 63-91352 | 4/1988 |
| WO | WO 91/11184 | 8/1991 |
| WO | WO 92/19226 | 11/1992 |
| WO | WO 93/21917 | 11/1993 |
| WO | WO 94/04138 | 3/1994 |
| WO | WO 94/20100 | 9/1994 |
| WO | WO 95/03791 | 2/1995 |
| WO | WO 95/22324 | 8/1995 |
| WO | WO 96/39133 | 12/1996 |
| WO | WO 97/29735 | 8/1997 |
| WO | WO 98/50044 | 11/1998 |
| WO | WO 99/37305 | 7/1999 |

OTHER PUBLICATIONS

Ascher, J.A. et al., 1995, "Bupropion: a review of its mechanism of antidepressant activity", J. Clin. Psych. 56:395–401.

Bannon et al., 1998, "Broad–spectrum, non–opoid analgesic activity by selective modulation of neuronal nicotinic acetylcholine receptors", Science 279:77–81.

Bischoff et al., 1984, "Affinity changes of rat striatal dopamine receptor in vivo after acute bupropion treatment", Eur. J. Pharmaco. 104:173–176.

Blondel–Hill et al., 1993, "Treatment of the chronic fatigue syndrome", Drugs 46(4):639–651.

Borowski, T.B. et al., 1993, "Amphetamine and antidepressant drug effects on GABA– and NMDA–related seizures", Brain Res. Bull. 30:607–610.

Calabrese, J.R. et al., 1991, "Treatment of depression", Primary Care 18(2):421–433.

Castaldi, G. et al., 1987, "Tartaric acid, an efficient chiral auxiliary: new asymmetric synthesis of 2–alkyl–2–arylacetic acids", J. Org. Chem. 52:3018.

Castello, R.A. and Mattocks, A.M., J. Pharm. Sci. 51(2):106–108 (1962).

Charney, D.S. et al, 1983, "Monoamine receptor sensitivity and depression: clinical studies of antidepressant effects on serotonin and noradrenergic function," Psychopharmacol. Bull 19(3):490.

(List continued on next page.)

Primary Examiner—William R. A. Jarvis
(74) Attorney, Agent, or Firm—Pennie & Edmonds LLP

(57) ABSTRACT

Methods are disclosed utilizing the optically pure (−)-isomer of bupropion, which is a potent drug for treating depression, Parkinson's disease, obesity, weight gain and other disorders.

10 Claims, No Drawings

OTHER PUBLICATIONS

Clay et al., 1988, "Clinical and neuropsychological effects of the novel antidepressant bupropion", Psycopharma. Bull. 24(1):143–148.
Conners, K.C. et al., 1996, "Bupropion hydrochloride in attention deficit disorder with hyperactivity", J. Am. Acad. Child Adolesc. Psychiatr. 34(10):1314–1321.
Cooke C.E., 1997, "Therapeutic advances in the treatment of cigarette addiction", J. Pharmacy Practice 10(5):329–337.
Cooper, B.R. et al., 1994, "Evidence that the acute behavioral and electrophysiological effects of bupropion (Wellbutrin®) are mediated by a noradrenergic mechanism", Neuropsychopharmacology 11(2):133–141.
Coutts, R.T. & Baker, G.B., 1989, "Implications of chirality and geometric isomerisms in some psychoactive drugs and their metabolites", Chirality 1:99–120.
Crenshaw et al., 1987, "Pharmacological modification of psychosexual dysfunction", J. Sex. Marital Ther. 13(4):239–252.
Cusack, B. et al., 1994, "Binding of antidepressants to human brain receptors: focus on newer generation compounds", Psychopharmacol. 114:559–565.
Davidson et al., 1994, "Bupropion in chronic low back pain", J. Clin. Psychiatry 55(8):362.
Dilsaver, S.C. et al., 1992, "The efficacy of bupropion in winter depression: results of an open trial", J. Clin. Psychiatry 53(7):252–255.
Eliel, E.L., 1962, *Stereochemistry of Carbon Compounds,* McGraw–Hill, NY.
Ferris, R.M. et al., 1983, "Studies of bupropion's mechanism of antidepressant activity", J. Clin. Psychiatry 44(5):74–78.
Ferris & Beaman, 1983, "Bupropion: a new antidepressant drug, the mechanism of action of which is not associated with down–regulation of postsynaptic β–adrenergic, serotonergic (5–$HT_2$), $α_2$–adrenergic, imipramine and dopaminergic receptors in brain", Neuropharmacol. 22(1):1257–1267.
Ferry, L.H. et al, 1992, "Enhancement of smoking cessation using the anti–depressant bupropion hydrochloride" (abstract) Circulation 86:671.
Ferry, L.H. et al., 1994, "Efficacy of bupropion for smoking cessation in non–depressed smokers," J. Addict, Dis. 13:A9.
Fisher, R.S., 1989, "Animal models of the epilepsies", Brain Res. Reviews 14:245–278.
Foote et al., 1984, "Proconvulsant effect of morphine on seizures induced by pentylenetetrazol in the rat", 105:179–184.
Garland et al., 1998, "Pharmacotherapy of adolescent attention deficit hyperactivity disorder: challenges, choices and caveats", J. Psychopharmacology 12(4):385–395.
Goetz et al., 1984, "Bupropion in Parkinson's Disease," 34:1092–4.
Goodnick, P.J., 1994, "Pharmacokinetic optimisation of therapy with newer antidepressants", Clin. Pharmacokinet. 27(4):307–330.
Goodnick, P.J. & Sandoval, R., 1993, "Psychotropic treatment of depression: results of an open trial", J. Clin. Psych. 54(1):13–20.
Green, A.R. & Murray, T.K., 1989, "A simple intravenous infusion method in rodents for determining the potency of anticonvulsants acting through GABAergic mechanisms", J. Pharm. Pharmacol. 41:879–880.
Grimes et al., 1996, "Spontaneous orgasm with the combined use of bupropion and sertraline", Soc. Biol. Psych. 40:1184–1185.
Handbook of Pharmaceutical Excipients, 2nd ed., Wade and Willer eds., pp. 257–259 (1994).
Hsyu, P.H. et al., 1997, "Pharmacokinetics of bupropion and its metabolites in cigarette smokers versus nonsmokers", J. Clin. Pharmacol. 37(8):737–743.
Hsyu, P.H. et al., Nov. 10, 1997 Chemical Abstracts 127(19): Abstract No. 257089; Columbus, Ohio.
Janowsky, A., et al., J. Neurochem. 46:1272–1276 (1986).
Kelley, J.L. et al., 1996, "(2S,3S,5R)–2–(3,5–difluoropheynl)–3,5–dimethyl–2–morpholinol: a novel antidepressant agent and selective inhibitor of norepinephrine uptake", J. Med. Chem. 39:347–349.
Ketter, T.A. et al., 1995, "Carbamazepine but not valproate induces bupropion metabolism", J. Clin. Psycopharmacol. 15(5):327–333.
Laizure, S.C. et al., 1985, "Pharmacokinetics of bupropion and its major basic metabolites in normal subjects after a single dose", Clin. Pharmacol. Ther. 38:586–589.
Lief, H.I., 1996, "Bupropion treatment of depression to assist smoking cessation", Am. J. Psychiatry 153(3):442.
Little, K.Y. et al., 1993, "[$^{125}$I]RTI–55 binding to cocaine–sensitive dopaminergic and serotonergic uptake sites in the human brain", J. Neurochem. 61:1996–2006.
Martin, P, et al., 1990, "Antidepressant Profile of Bupropion and Three Metabolites in Mice," Pharmacopsychiatry 23:187–194.
McNamee et al., 1986, "Stimulation of substrate oxidation in rat hepatic mitochondria following pretreatment with appetite modifying drugs", J. Pharm. Pharmacol. 37:147.
Merskey, H., 1965, "The effect of chronic pain upon the response to noxious stimuli by psychiatric patients," J. Psychosom. Res. 8:405–419.
Michell, G.F. et al., 1989, "Effect of bupropion on chocolate craving", Am. J. Psychiatry 146(1):119–120.
Michell, G.F. et al., 1989, "Dr, Mitchell and associates reply", Am. J. Psychiatry 146(8):1089.
Moisset, B., et al., Brain Res. 92:157–164 (1975).
Moret, C. & Brile, M., 1988, "Sensitizing of the response of 5–HT autoreceptors to drugs modifying synaptic availability of 5–HT", 27(1):43–49.
Musso et al., 1993, "Synthesis and evaluation of the antidepressant activity of the enantiomers of bupropion", Chirality 5:495–500.
Musso et al., 1997, "Synthesis and Evaluation of the Anticonvulsant Activity of a Series of 2–Amino–Phenyl–1–Propanols Derived from the Metabolites of the Antidepressant Bupropion," Bioorganic & Medical Chemistry Letters, vol. 7 No. 1, pp. 1–6, 1997.
Nomikos et al., 1992, "Effects of chronic bupropion on interstitial concentrations of dopamine in rat nucleus accumbens and striatum", Neuropsychopharmacology 7(1):7–14.
Nutt, D.J. et al., 1981, "Studies on the postietal rise in seizure threshold," Eur. J. Pharmacol. 71:287–295.
Nutt, D.J. Et al, 1980, "On the measurement in rats of the convulsant effect of drugs and the changes which follow electroconvulsive shock," Neuropharmacology 19:1017–1023.
Olsen et al., 1985, "Benzodiazepine/γ–aminobutyric acid receptor deficit in the midbrain of the seizure–susceptible gerbil", PNAS USA 82:6701–6705.

Pearlstein et al., 1997, "Comparison of fluoxetine, bupropion, and placebo in the treatment of premenstrual dysphoric disorder", J. Clin. Psychopharmacol. 17(4):261–266.

Physician's Desk Reference®, 1998, pp. 1120–1127.

Popli, A.P. et al., 1994, "Antidepressant–associated seizures", J. Clin. Psych. 55(6):267.

Popli, A. et al., 1995, "Bupropion and anticonvulsant drug interactions", Annals of Clin. Psychiatr. 7(2):99–101.

Posner, J. et al., 1985, "The disposition of bupropion and its metabolites in healthy male volunteers after single and multiple doses", Eur. J. Clin. Pharmacol. 29:97–103.

Potter, W.Z. & Manji, H.K., 1990, "Antidepressants, metabolites, and apparent drug resistance", Clin. Neuropharmacol. 13(1):S45–S53.

Remingtons: The Practice of the Science and Pharmacy, 19th ed., Gennaro, ed., p. 1625 (1995).

Rose, J.E., 1996, "Nicotine addiction and treatment", Annu. Rev. Med. 47:493–507.

Rosenstein, D.L. et al., 1993, "Seizures associated with antidepressants: a review", J. Clin. Psychiatry 54(8):289–299.

Rudorfer, M.V. et al., 1994, "Comparative tolerability profiles of the newer versus older antidepressants", Drug Safety 10(1):18–46.

Schroeder, D.H., 1983, "Metabolism and kinetics of bupropion", J. Clin. Psychiatr. 44(5):79–81.

Schroedger, D.H. et al., 1979, "The isolation and identification of some basic urinary metablites of bupropion—HCL in man", The Pharmacologist 21(3):191.

SCRIP Itraconazole for pulse dosing of onychomycosis, Dec. 18, 1996.

Stathis, M. et al., 1995, "Rate of binding of various inhibitors at the dopamine transporter in vivo", Psychopharmacol. 119:376–384.

Storrow, A.B., 1994, "Bupropion overdose and seizure", Am. J. Emerg. Med. 12:183–184.

Suckow, R.F. et al.,1986, "Pharmacokinetics of bupropion and metabolites in plasma and brain of rats, mice, and guinea pigs", Drug Metab. Disposit. 14(6):692–697.

Suckow, R.F. et al., 1997, "Enantiomeric determination of the phenylmorpholinol metabolite of bupropion in human plasma using coupled achiral–chiral liquid chromatography", Biomedical Chromatog. 11:174–179.

Sulser, F., 1983, "Molecular mechanism in antidepressant action," *Psychopharmacol.* Bull. 19(3):300.

Sweet, R.A. et al., 1995, "Pharmacokinetics of single– and multiple– dose bupropion in elderly patients with depression", J. Clin. Pharmacol. 35:876–884.

Testa B. and Trager, W.F., 1990, "Racemates Versus Enantiomers in Drug Development: Dogmatism or Pragmatism?" Chirality 2:129–133.

Vassout, A. et al., 1993, "Regulation of dopamine receptors by bupropion: comparison with antidepressants and CNS stimulants", J. Receptor Res. 13(1–4):341–354.

Ward, N.G., 1990, *The Management of Pain,* Second Edition, vol. 1, Chapter 18 (eds.) Bonica, J.J. pp. 310–319.

Ward, R. et al., 1971, "Asymmetric audiogenic seizures in mice: a possible analogue of focal epilepsy", Brain Res. 31:207–210.

Welch, R.M. et al., 1987, "Pharmacological significance of the species differences in bupropion metabolism", Nenobiotica 17(3):287–298.

Wilen, S.H., 1972, *Tables of Resolving Agents and Optical Resolutions,* Univ. of Notre Dame Press, Notre Dame, IN.

Wright et al., 1985, "Bupropion in the long–term treatment of cyclic mood disorders: mood stabilizing effects", J. Clin. Psych. 46(1):22–25.

Zarrindast et al., 1988, "Anorectic and behavioral effects of bupropion", Gen. Pharmacology 19(2):201–204.

Stathis, M. et al., 1995, "Rate of binding of various inhibitors at the dopamine transporter in vivo", Psychopharmacol. 119:376–384.

METHODS FOR TREATING DEPRESSION AND OTHER DISORDERS USING OPTICALLY PURE (−)-BUPROPION

This is a Divisional of Ser. No. 09/891,266, filed Jun. 27, 2001 now U.S. Pat. No. 6,369,113, which is a Divisional of Ser. No. 09/553,029, filed Apr. 20, 2000 now U.S. Pat. No. 6,277,887, which is a Divisional of Ser. No. 09/238,812, filed on Jan. 28, 1999 now U.S. Pat. No. 6,110,973 which claims benefit of provisional application No. 60/072,931 filed Jan. 29, 1998.

FIELD OF THE INVENTION

This invention relates to methods of treatment and pharmaceutical compositions employing the compound (−)-bupropion.

BACKGROUND OF THE INVENTION

Steric Relationships and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 16 of the 20 most prescribed drugs exhibit chirality. A case in point is provided by the L-form of the β-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer was a potent teratogen.

Bupropion is available only as a racemic mixture called Wellbutrin® and Wellbutrin® (for depression), and Zyban® (to achieve smoking cessation). That is, bupropion is available as a mixture of optical isomers, called enantiomers. The racemic mixture of bupropion which is commercially available is administered as a hydrochloride salt. In addition, European Patent Application No. 84101070.5 published Sept. 12, 1984 discloses the benefits of bupropion maleate over bupropion hydrochloride.

Bupropion is used primarily in the treatment of depression, which along with mania, falls under the heading of affective disorders. Particularly, bupropion is used in patients who do not respond to, or cannot tolerate other antidepressants, such as the tricyclic agents or monoamine oxidase inhibitors. Additionally, the racemic mixture of bupropion is useful in the management of patients with bipolar and schizo-affective disorder, attention-deficit disorder, psycho-sexual dysfunction, bulimia and other eating disorders, and Parkinson's disease.

Affective disorders, including major depression, and the bipolar, manic-depressive illness, are characterized by changes in mood as the primary clinical manifestation. Major depression is the most common of the significant mental illnesses, and it must be distinguished clinically from periods of normal grief, sadness and disappointment, and the related dysphoria or demoralization frequently associated with medical illness. Depression is characterized by feelings of intense sadness, and despair, mental slowing and loss of concentration, pessimistic worry, agitation, and self-deprecation. Physical changes can also occur, including insomnia, anorexia, and weight loss, decreased energy and libido, and disruption of hormonal circadian rhythms. Often the condition responds well to tricyclic or related antidepressant drugs, monoamine oxidase inhibitors, or in resistant cases or severe disease, to electro-convulsive shock treatment.

Mania, as well as depression, is characterized by changes in mood as the primary symptom. Either of these two extremes of mood may be accompanied by psychosis with disordered thought and delusional perceptions. Psychosis may have, as a secondary symptom, a change in mood, and it is this overlap with depression that causes much confusion in diagnosis. Severe mood changes without psychosis frequently occur in depression and are often accompanied by anxiety.

Through an unknown mechanism of action, bupropion has been demonstrated to be an effective treatment in depression in short-term and longer duration clinical studies. The racemic mixture of bupropion has been reported to have an antidepressant activity equal to amitriptyline, the tricyclic antidepressant, with fewer anticholinergic, sedative and cardiovascular side effects than with amitriptyline.

Parkinson's disease, independent of a specific etiology, is a chronic, progressive central nervous system disorder which usually appears insidiously in the latter decades of life. The disease produces a slowly increasing disability in purposeful movement. It is characterized by four major clinical features of tremor, bradykinesia, rigidity and a disturbance of posture. Often patients have an accompanying dementia. In idiopathic Parkinsonism, there is usually a loss of cells in the substantia nigra, locus ceruleus, and other pigmented neurons of the brain, and a decrease of dopamine content in nerve axon terminals of cells projecting from the substantia nigra. The understanding that Parkinsonism is a syndrome of dopamine deficiency and the discovery of levodopa as an important drug for the treatment of the disease were the logical culmination of a series of related basic and clinical observations, which serves as the rationale for drug treatment.

When the racemic mixture of bupropion is used to treat Parkinson's disease, an improvement in gait, akinesia, and postural stability were observed, with tremor improving in those patients experiencing the most global benefit. Concomitant depression was alleviated in several of the patients reporting the condition.

Attention-deficit disorder ("ADD") is a common behavioral learning disorder in children which adversely affects school performance and family relationships. Symptoms and signs include hyperactivity (e.g., ADDH and AD/HD, DSM-IV), impulsivity, emotional lability, motor incoordination and some perceptual difficulties. Treatment has included psychostimulants, which while effective are controversial, and may cause troubling side effects such as dysphoria, headache and growth retardation. Other drugs, including the tricyclic antidepressants, appear to improve attention, but may be less effective than the psychostimulants.

Bupropion has been shown to be effective in children with attention-deficit disorder or conduct disorder thus improving the symptoms of anxiety, hostility and uncooperativeness, antisocial behavior, as well as eating disturbances. The drug has also demonstrated activity in cases of psycho-sexual dysfunction and bulimia. However, bupropion is contraindicated in patients with a seizure disorder, or a current or prior diagnosis of bulimia or anorexia nervosa characterized by a disturbed sense of body image and abnormally high anxiety about weight gain.

It has been suggested that the racemic mixture of bupropion could be used to assist in weight loss. Treatment with bupropion is consistently associated with a lack of weight gain. Also bupropion reduces episodes of binge eating and purging. Although the mechanism by which bupropion causes weight loss is uncertain, an increase in the activity of the patient may play some part together with subtle changes in food intake and metabolism.

The causes of excess body weight and/or obesity are complex; however, a common denominator in the overweight person's diet is a caloric intake which exceeds that person's body expenditures. One method of treating a person who is overweight and/or obese is to restrict that person's caloric intake, in combination with an exercise regimen. This method may be limited in its effectiveness since many overweight or obese people have developed eating and activity patterns which are counterproductive to achieving weight reduction. Another method to treat overweight or obese patients is to administer appetite suppressant drugs in conjunction with a weight reduction program. The drawback to this method is that many appetite suppressant drugs produce undesirable adverse effects which limit their usefulness.

The racemic mixture of bupropion, in addition to its use in the treatment of depression and the other above-mentioned disorders, has been shown to have a wide spectrum of action which includes:

Treatment of the effects of ethanol (U.S. Pat. No. 4,393,078)

Treatment of Tardine Dyskinesia (U.S. Pat. No. 4,425,363)

Treatment of Minimal Brain Dysfunction (U.S. Pat. No. 4,435,449)

Treatment of amelioration of prostate hypertrophy and sexual dysfunction (U.S. Pat. No. 4,835,147)

Treatment of psychostimulant addiction (U.S. Pat. No. 4,935,429)

Treatment of Psychosexual Dysfunction (U.S. Pat. No. 4,507,323)

Methods of Reducing Cholesterol (U.S. Pat. No. 4,438,138)

Methods of assisting weight loss (U.S. Pat. No. 4,895,845)

The racemic mixture of bupropion has been shown to have certain advantages over other antidepressant drugs. For example, bupropion does not inhibit monoamine oxidase, or block the reuptake of serotonin. At therapeutic concentrations, the compound presumably does not bind to adrenergic, dopamine, GABA, histamine, muscarinic, serotonin, or imipramine binding sites. While its specific neurochemical antidepressant action is unknown, it does have a relatively weak effect on blocking the reuptake of dopamine, and it appears to reduce norepinephrine metabolism.

While the racemic mixture of bupropion has advantages, it also has disadvantages. Among these disadvantages are adverse effects in addition to those described above. The most serious adverse effect associated with the racemic mixture of bupropion is the increased incidence of seizures.

In addition, other frequently reported adverse effects associated with the use of racemic bupropion include nausea, vomiting, excitement, agitation, blurred vision, restlessness, postural tremor, and some hallucinations/confusional states with the potential for abuse. Other adverse or side effects associated with the racemic mixture of bupropion include but are not limited to anxiety, insomnia, headaches and/or migraines, dry mouth, constipation, tremor, sleeping disturbances, dermatologic problems (e.g., rashes), neuropsychiatric signs and symptoms (e.g., delusions and paranoia), and weight loss or gain. See, the Physician's. Desk Reference® (1998). These effects are dose limiting in a number of patients. In Parkinsonian patients, the adverse effects can be the particular toxicity. of the racemic mixture of bupropion, or the result of a drug interaction (as most patients were receiving concomitant levodopa).

Thus, it is desirable to find a compound with the advantages of the racemic mixture of bupropion without the above-described disadvantages.

SUMMARY OF THE INVENTION

The active compound of compositions and methods disclosed herein is an optical isomer of the compound bupropion which is described in U.S. Pat. Nos. 53,819,706 and 3,885,046. Chemically, this isomer is (−)-2-(tertbutylamino)-3'-chloropropiophenone or (−)-1-(3-chlorophenyl)-2[(1,1-dimethyl-ethyl)amino]-1-propanone. This isomer will hereinafter be referred to as "(−)-bupropion", which also includes the substantially optically pure (−)-bupropion isomer.

It has now been discovered that the optically pure (−)-isomer of bupropion is an effective antidepressant which is useful in treating depression in humans. In accordance with the present invention, (−)-bupropion can be used to treat depression while avoiding adverse effects including but not limited to seizures, agitation, dry mouth, insomnia, headache/migraine, nausea, dizziness, tachycardia, vomiting, constipation, and tremor associated with the racemic mixture of bupropion. It has also been discovered that (−)-bupropion and pharmaceutical compositions containing optically pure (−)-bupropion are useful in treating weight gain or obesity. Furthermore, it has been discovered that the optically pure (−)-isomer of bupropion is useful in the treatment of Parkinson's disease. In addition, it has been found that the optically pure (−)-isomer of bupropion is useful in the treatment of other disorders including but not limited to bipolar disorders, attention-deficit disorders, conduct disorders, psycho-sexual dysfunction, bulimia, eating disorders and specific food cravings.

The present invention also includes methods for treating the above-described conditions in a human while avoiding adverse effects that are associated with the racemic mixture of bupropion, by administering the optically pure (−)-isomer of bupropion to said human.

DETAILED DESCRIPTION OF THE INVENTION

The present invention encompasses a method of treating depression in a human while avoiding the concomitant liability of adverse effects associated with the administration of racemic bupropion which comprises administering to said human in need of antidepressant therapy, an amount of (−)-bupropion or a pharmaceutically acceptable salt thereof, substantially free of its (+)-stereoisomer, said amount being sufficient to alleviate depression, but insufficient to cause adverse effects associated with racemic bupropion.

The present invention also encompasses pharmaceutical compositions for the treatment of humans which comprises a therapeutically effective amount of (−)-bupropion or a pharmaceutically acceptable salt thereof, substantially free of its (+)-stereoisomer, and a pharmaceutically acceptable carrier. Preferred pharmaceutical compositions are those which have a means for controlled sustained release of the active ingredient, (−)-bupropion.

The present invention further encompasses a method of treating Parkinson's disease in a human while avoiding the concomitant liability of adverse effects associated with the administration of racemic bupropion, which comprises administering to said human suffering from Parkinson's disease, an amount of (−)-bupropion, or a pharmaceutically acceptable salt thereof, substantially free of its (+)-stereoisomer, said amount being sufficient to alleviate said condition, but insufficient to cause adverse effects associated with administration of racemic bupropion.

Further, the present invention encompasses a method of treating obesity or weight gain in a human, which comprises administering to said human in need of a reduction in weight, an amount of (−)-bupropion or a pharmaceutically acceptable salt thereof, substantially free of its (+)-stereoisomer said amount being sufficient to reduce weight or prevent weight gain, but insufficient to cause adverse effects associated with administration of racemic bupropion.

The present invention also encompasses a method of treating disorders including, but not limited to, bipolar disorders, attention-deficit disorders, conduct disorders, psycho-sexual dysfunction, bulimia, eating disorders and specific food cravings in humans while avoiding the concomitant liability of adverse affects associated with the administration of racemic bupropion, which comprises administering to a human in need of such therapy a therapeutically effective amount of (−)-bupropion, or a pharmaceutically acceptable salt thereof, substantially free of its (+)-stereoisomer.

The racemic mixture of bupropion (i.e., approximately a 50:50 mixture of its two enantiomers) causes antidepressant activity and provides therapy and/or reduction of symptoms in a variety of conditions and disorders; however, this racemic mixture, while offering the expectation of efficacy, causes a broad range of adverse effects. Utilizing the optically pure (−)-isomer of bupropion results in clearer dose-related definitions of efficacy, diminished adverse effects, and accordingly an improved therapeutic index. It is therefore, more desirable to use the (−)-isomer of bupropion for the conditions described herein.

The term "adverse effects" as used herein includes, but is not limited to seizures, dry mouth, insomnia, dizziness, restlessness, anxiety, agitation, headache/migraine, nausea/vomiting, constipation, tremor, delusions, tachycardia, hallucinations, psychotic episodes, blurred vision, confusion, paranoia, rashes and sleep disturbances.

The term "substantially free of the (+)-stereoisomer" as used herein means that the composition contains a greater proportion of the (−)-isomer of bupropion in relation to the (+)-isomer of bupropion. In a preferred embodiment the term "substantially free of its (+)-isomer" as used herein means that the composition contains at least 90% by weight of (−)-bupropion and 10% by weight or less of (+)-bupropion; or more preferably about 95% by weight of (−)-bupropion and 5% or less of its (+)-isomer. These percentages are based on the total amount of bupropion present in the composition. In the most preferred embodiment the term "substantially free of the (+)-stereoisomer" means that the composition contains approximately 99% by weight of (−)-bupropion, and 1% or less of the (+)-bupropion. In another preferred embodiment, the term "substantially free of its (+)-stereoisomer" as used herein means that the composition contains greater than 99% by weight of the (−)-isomer of bupropion, again based on the total amount of bupropion present. The terms "substantially optically pure (−)-isomer of bupropion," "optically pure (−)-isomer of bupropion" and "(−)-isomer of bupropion" are also encompassed by the above-described amounts.

The term "a method of treating depression" as used herein means relief from the symptoms of depression which include, but are not limited to changes in mood, feelings of intense sadness and despair, mental slowing, loss of concentration, pessimistic worry, agitation, and self-deprecation. Physical changes may also be relieved, including insomnia, anorexia and weight loss, decreased energy and libido, and the return of normal hormonal circadian rhythms.

The term "attention deficit disorder" (ADD) and "attention deficit disorder with hyperactivity" (ADDH), DSM-III, or attention deficit/hyperactivity disorder (AD/HD), DSM-IV are used herein mean in accordance with the accepted meanings.

The term "treating Parkinson's disease" as used herein means relief from the symptoms of Parkinson's disease which include, but are not limited to tremor, bradykinesia, rigidity, and a disturbance of posture.

The term "treating obesity or weight gain in a human" as used herein means reduction of weight or relief from being overweight or gaining weight due to extensive consumption of food and other factors including metabolism disorders.

Synthesis of Optically Pure Bupropion

The synthesis of the (−)-isomer of bupropion may start from readily available 3-chloropropiophenone (1). Reaction of (1) with a (2R,3R)-(+)-dialkyl tartrate such as (+)-dimethyl or diethyl tartrate in the presence of an acid catalyst such as methanesulfonic acid gives the chiral acetal (2) according to Castaldi (G. Castaldi, et al., *J. Org. Chem.* 1987, 52: 3018). Steroselective bromination with bromine in carbon tetrachloride, or alternatively ethyl acetate, then produces the corresponding bromoacetal (3) as the major product according to the above-referenced procedure developed by Castaldi and co-workers. The bromoacetal (3) is purified by column chromatography to yield the optically pure bromoacetal (3) which is then hydrolyzed in the presence of an acid to afford the bromoketone (4). Treatment of the bromoketone (4) with tert-butylamine, followed by reaction with anhydrous hydrogen chloride, then produces optically pure (−)-bupropion hydrochloride (5) after. recrystallization. See the scheme below.

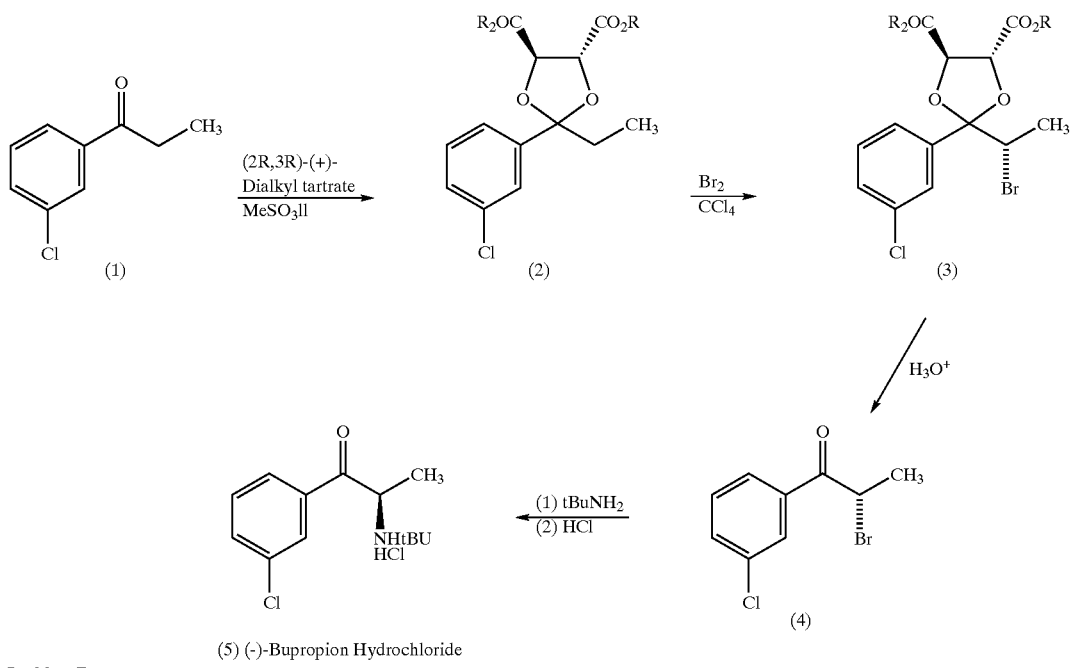

(5) (-)-Bupropion Hydrochloride

R = Me or Et

Alternatively, the optically pure isomers of bupropion can be prepared asymmetrically according to the procedures reported by Musso et al., "Synthesis and Evaluation of the Antidepressant Activity of the Enantiomers of Bupropion", *Chirality* 5:495–500 (1993) which is incorporated herein by reference in its entirety.

In addition to the above-described methods the stereoisomers of bupropion may be obtained by resolutions of a mixture of enantiomers of bupropion using conventional means such as an optically active resolving agent; see, for example, "Stereochemistry of Carbon Compounds", by E. L. Eliel (McGraw-Hill, NY, 1962), and S. H. Wilen, p. 268 in "Tables of Resolving Agents and Optical Resolutions" (E. L. Eliel, Ed., Univ. of Notre Dame Press, Notre Dame, Ind., 1972).

The magnitude of a prophylactic or therapeutic dose of (−)-bupropion in the acute or chronic management of disease will vary with the severity of the condition to be treated and its route of administration. The dose and dose frequency will also vary according to the age, weight, condition and response of the individual patient. In general, the recommended daily dose range for the conditions described herein lies within the range of from about 10 mg to about 750 mg per day, generally divided equally into doses given three or four times a day. Preferably, a daily dose range should be between 50 mg and 600 mg per day, usually divided equally into a three or four times a day dosing. Most preferably, a daily dose range should be between 60 mg and 450 mg per day, usually divided equally into a three times or a four times a day dosing. It may be necessary to use dosages outside these ranges in some cases. The physician will know how to increase, decrease or interrupt treatment based upon patient response. The various terms described above such as "said amount being sufficient to alleviate said depression", "said amount being sufficient to alleviate said condition" when said condition is Parkinson's Disease, "said amount being sufficient to reduce weight or weight gain", "said amount being sufficient to achieve weight loss" and "therapeutically effective amount" are encompassed by the above-described dosage amounts and dose frequency schedule.

Any suitable route of administration may be employed for providing the patient with an effective dosage of (−)-bupropion. For example, oral, rectal, parenteral, transdermal, subcutaneous, intrathecal, intramuscular and the like may be employed as appropriate. Dosage forms include tablets, coated tablets, caplets, capsules, troches, dispersions, sustained release formulations, suspensions, solutions, patches and the like.

The pharmaceutical compositions of the present invention comprise the (−)-isomer of bupropion as active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids including inorganic and organic acids. Such acids include maleic, acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are hydrobromic, hydrochloric, phosphoric, and sulfuric acids.

The pharmaceutical compositions of the present invention include compositions suitable for oral, rectal, and parenteral administration (including subcutaneous, intrathecal, intramuscular, and intravenous), although the most suitable route in any given case will depend on the nature and severity of the condition being treated. The most preferred route of the present invention is the oral route. They may be conveniently presented in unit dosage form and prepared by any of the methods well-known in the art of pharmacy.

In the case where an oral composition is employed, a suitable dosage range for use is, e.g., from about 10 mg to about 750 mg per day, generally divided equally into a three times a day dosing, preferably from about 50 mg to about 600 mg per day, generally divided equally into a three times a day dosing and most preferably from about 60 mg to about 450 mg per day, generally divided equally into a three times a day dosing. Patients may be upward titrated from below to within this dose range to a satisfactory control of symptoms as appropriate.

In practical use, (−)-bupropion can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous injections or infusions). In preparing the compositions for oral dosage form, any of the usual pharmaceutical media may be employed, for example, water, glycols, oils, alcohols, flavoring agents, preservatives, coloring agents and the like in the case of oral liquid preparations, for example, suspensions, elixirs and solutions; or aerosols; or carriers such as starches, sugars, microcrystalline cellulose, stabilizers, diluents, granulating agents, lubricants, binders, fillers, disintegrating agents and the like in the case of oral solid preparations such as, powders, capsules and tablets, with the solid oral preparations being preferred over the liquid preparations. The preferred solid oral preparation is tablets. The most preferred solid oral preparation is coated tablets. Because of their ease of administration tablets and capsules represent the most advantageous oral dosage unit form, in which case solid pharmaceutical carriers are obviously employed. If desired, tablets may be coated by standard aqueous or nonaqueous techniques.

Pharmaceutical stabilizers may also be used to stabilize compositions containing (−)-bupropion or salts thereof; acceptable stabilizers including but are not limited to L-cysteine hydrochloride, glycine hydrochloride, malic acid, sodium metabsulfite, citric acid, tartaric acid and L-cysteine dihydrochloride. See, e.g., U.S. Pat. No. 5,358,970 which is incorporated herein by reference.

In addition to the common dosage forms set out above, the compounds of the present invention may also be administered by controlled release or sustained release means and/or delivery devices such as those described in U.S. Pat. Nos. 3,845,770; 3,916,899; 3,536,809; 3,598,123; 3,630,200; 4,008,719, 4,687,660, and 4,769,027, the disclosures of which are hereby incorporated by reference. Preferred controlled release or sustained released tablets for use with (−)-bupropion are described in U.S. Pat. No. 5,427,798 which is incorporated herein by reference.

Pharmaceutical compositions of the present invention suitable for oral administration may be presented as discrete units such as capsules, cachets, or tablets or aerosol sprays, each containing a predetermined amount of the active ingredient, as a powder or granules or as a solution or a suspension in an aqueous liquid, a non-aqueous liquid, an oil-in-water emulsion, or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, filler, lubricant, inert diluent, and/or surface active or dispersing agent. Molded tablets may be made by molding in a suitable machine a mixture of the powdered compound moistened with an inert liquid diluent. Desirably, each tablet contains from about 10 mg to about 250 mg of the active ingredient, and each cachet or capsule contains from about 10 mg to about 250mg of the active ingredient. Most preferably, the tablet, cachet or capsule contains one of four dosages: about 50 mg, about 75 mg, about 100 mg and about 150 mg of active ingredient.

The invention is further defined by reference to the following examples describing in detail the preparation of the compound and compositions of the present invention. It will be apparent to those skilled in the art that many modifications, both to materials and methods, may be practiced without departing from the purpose and interest of this invention.

All temperatures are in degrees Celsius.

EXAMPLES

Example 1

ORAL FORMULATION
Coated Tablets:

| Formula | Quantity per Tablet (mg.) |
|---|---|
| (−)-bupropion | 75 |
| Lactose | 125 |
| Corn Starch | 5.0 |
| Water (per thousand Tablets) | 30.0 ml* |
| Magnesium Stearate | 0.5 |
| Corn Starch | 25.0 |

*The water evaporates during manufacture.

The active ingredient is blended with the lactose until a uniform blend is formed. The smaller quantity of corn starch is blended with a suitable quantity of water to form a corn starch paste. This is then mixed with said uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous techniques.

Example 2

ORAL FORMULATION
Capsules:

| Formula | Quantity per capsule in mg. | | |
|---|---|---|---|
| | A | B | C |
| Active ingredient (−)-bupropion | 25 | 50 | 75 |
| Lactose | 149.5 | 124.5 | 374 |
| Corn Starch | 25 | 25 | 50 |
| Magnesium Stearate | 0.5 | 0.5 | 1.0 |
| Compression Weight | 200.0 | 200.0 | 500.0 |

The active ingredient, (−)-bupropion, lactose, and corn starch are blended until uniform; then the magnesium stearate is blended into the resulting powder. The resulting mixture is encapsulated into suitably sized two-piece hard gelatin capsules.

Example 3

ORAL FORMULATION
Tablets

| Formula | Quantity per Tablet in mg. | | |
|---|---|---|---|
| | A | B | C |
| Active ingredient, (−)-bupropion | 20 | 40 | 100 |
| lactose BP | 134.5 | 114.5 | 309.0 |
| starch BP | 30.0 | 30.0 | 60.0 |
| Pregelatinized Maize Starch BP | 15.0 | 15.0 | 30.0 |
| Magnesium stearate | 0.5 | 0.5 | 1.0 |
| Compression Weight | 200.0 | 200.0 | 500.0 |

The active ingredient is sieved through a suitable sieve and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to lactose or the compression weight and using punches to suit.

Example 4

Sustained Release Formulation (Tablet)

| FORMULA | QUANTITY PER TABLET (mg) |
|---|---|
| (−)-bupropion hydrochloride | 100 |
| Contramid ® crosslinked amylose | 98.8 |
| Cysteine hydrochloride | 7.5 |
| Magnesium stearate | 1.2 |

(−)-Bupropion Hydrochloride is formulated using Contramid® (Labopharm, Inc, Quebec) technology. The formulation is prepared by blending the ingredients above (dry) and compressing into tablets. Alternatively, the ingredients can be formulated using wet granulation technology known in the art. (See Example 1).

Example 5

Sustained Release Formulation (Tablet)

| FORMULA | QUANTITY PER TABLET (mg) |
|---|---|
| Contramid ® crosslinked amylose | 98.8 |
| Cysteine hydrochloride | 7.5 |
| (−)-bupropion hydrochloride | 75 |
| Magnesium stearate | 1.2 |

(−)-Bupropion Hydrochloride is formulated using Contramid® (Labopharm, Inc, Quebec), technology. The formulation is prepared by blending the ingredients above (dry) and compressing into tablets. Alternatively, the ingredients can be formulated using wet granulation technology known in the art. (See Example 1).

Example 6

| FORMULA | QUANTITY PER TABLET (mg) |
|---|---|
| (−)-bupropion hydrochloride | 150 |
| Diffutab ® hydrophilic polymer mixture | 100 |
| Microcrystalline cellulose | 100 |
| Cysteine hydrochloride | 7.5 |
| Magnesium stearate | 4 |

(−)-Bupropion Hydrochloride is formulated using Diffutab® (Eurand, Microencapsulation, S.A. of Switzerland) technology. The formulation components are dry blended and directly compressed into tablets or formulated using wet granulation technology.

The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference.

Other embodiments are within the following claims.

What is claimed is:

1. A method of treating a disorder selected from the group consisting of bipolar disorders, attention-deficit disorders, conduct disorders, psycho-sexual dysfunction, bulimia eating disorders and specific food craving which comprises administering to a human suffering from said disorder a therapeutically effective amount of (−)-bupropion, or a pharmaceutically acceptable salt therefore, substantially free of its (+)-stereoisomer.

2. The method of claim 1 wherein (−)-bupropion is administered by intravenously, transdermally, or orally.

3. The method of claim 2 wherein (−)-bupropion is administered orally as a tablet or a capsule.

4. The method of claim 1 wherein the amount administered is from about 10 mg. to about 750 mg.

5. The method of claim 4 wherein the amount administered is from about 50 mg to about 600 mg.

6. The method of claim 5 wherein the amount administered is from about 60 mg to about 450 mg.

7. The method of claim 1 wherein the amount of (−)-bupropion or a pharmaceutically acceptable salt thereof is greater than approximately 90% by weight of the total amount of bupropion.

8. The method of claim 1 wherein the amount of (−)-bupropion or a pharmaceutically acceptable salt thereof, substantially free of its (+)-stereoisomer, is administered together with a pharmaceutically acceptable carrier.

9. The method according to claim 1 wherein (−)-bupropion is administered as the hydrochloride salt.

10. The method of claim 1 wherein (−)-bupropion is administered in a controlled or sustained release formulation.

* * * * *